United States Patent [19]

Pásztor et al.

[11] Patent Number: 4,551,132
[45] Date of Patent: Nov. 5, 1985

[54] PHARMACEUTICALLY ACCEPTABLE SILICON RUBBER AND THERAPEUTICAL SET AND THE USE THEREOF FOR SURGICAL EMBOLIZATION

[76] Inventors: Emil Pásztor, 4, Rákóczi-u, Budapest, Hungary, 1072; László Lázár, 4, Rózsahegy-u, Budapest, Hungary, 1024; József Nagy, 46/b, Törökbálinti-u, Budapest, Hungary, 1122; Katalin Pállosy née Becker, 31, Vincellûr-u, Budapest, Hungary, 1113

[21] Appl. No.: 445,690

[22] Filed: Dec. 1, 1982

Related U.S. Application Data

[62] Division of Ser. No. 235,084, Feb. 17, 1981, Pat. No. 4,429,062.

[30] Foreign Application Priority Data

Feb. 18, 1980 [HU]  Hungary ................. 369/80

[51] Int. Cl.⁴ ............................................. A61B 17/12
[52] U.S. Cl. ......................................... 604/52; 604/53; 604/96; 604/98; 128/325
[58] Field of Search ................. 604/96–103, 604/52–53; 128/325, 656–658

[56] References Cited

U.S. PATENT DOCUMENTS

| | | | |
|---|---|---|---|
| 3,687,142 | 8/1972 | Leibinzohn | 128/658 |
| 3,834,394 | 9/1974 | Hunter et al. | 604/99 |
| 4,196,731 | 4/1980 | Laurin et al. | 128/658 |
| 4,346,712 | 8/1982 | Handa et al. | 128/325 |

OTHER PUBLICATIONS

White, R. I., Kaufman, S. L., Barth, K. H. et al., JAMA 241 (12) Mar. 23, 1979.

Primary Examiner—C. Fred Rosenbaum
Assistant Examiner—Sherri E. Vinyard
Attorney, Agent, or Firm—Toren, McGeady, Stanger, Goldberg & Kiel

[57] ABSTRACT

A silicon rubber embolization agent used in general as well as cerebral vascular surgery having a component A which is composed of: a linear, low viscosity polysiloxane selected from the group consisting of dialkyl, alkylaryl, alkenylalkyl, and diarylpolysiloxanes having reactive functional groups selected from the group consisting of hydroxyl, acyloxyl, alkoxyl and amino; a low viscosity cyclic dialkylpolysiloxane having the formula $[R_2SiO]_4$, wherein R is alkyl; a pharmaceutically acceptable iodo-containing organosilicium; or a non-metallic, organic X-ray contrast material, and a component B which is a therapeutically acceptable cross-linking catalyst.

1 Claim, No Drawings

PHARMACEUTICALLY ACCEPTABLE SILICON RUBBER AND THERAPEUTICAL SET AND THE USE THEREOF FOR SURGICAL EMBOLIZATION

This is a division of application Ser. No. 235,084, filed Feb. 17, 1981, now U.S. Pat. No. 4,429,062.

BACKGROUND OF THE INVENTION

The present invention relates to a new silicon rubber mixture, its use for embolization as well as a therapeutic set containing the said mixture. The new mixture and the therapeutic equipment can be used for the first time in the cerebrovascular surgery and general surgery, respectively, for surgical embolization by the aid of a catheter.

Due to their localization or size certain parts of the human arterial system cannot be reached either via direct surgical exposure or endovascular approach, i.e. by means of the generally used rigid "Seldinger type" catheters (secondary and tertiary arteries). This problem has been solved by the use of balloon catheters of a diameter less than 1 mm. These flexible catheters are provided with an inflatable natural rubber balloon head, which can utilize the so-called "parachute-effect" of the blood stream. These balloon-catheters have particular importance for the cerebral endovascular surgery.

The cerebral arteries are surrounded by a stiff bony wall on the cranial base and have "syphons". Thus, the intracranial arteries become available only by using such catheters. The microcatheter filled with X-ray contrast medium, measurable by means of fluoroscopic screen, gives the possibility to follow exactly the position of the balloon-head. When using two or special balloon catheters at the same time, the catheter can also be directed into the secondary arteries. However, the above method is of diagnostic importance only, because the catheter when sent to its destination is left for blocking, it will also block the functionally important main vessels due to secondary thrombosis. This complication can be eliminated if the balloon were left in the vessels isolated, by detaching and withdrawing the catheter. The isolation and the so-called "superselective" embolization is ensured by the physical possibility that the inflated balloon head which is fixed to the inner wall of the vessel to be blocked is stronger than the flexible connection between the balloon and the ending of the catheter. However, the detachment of the balloon head, filled with fluid, is dangerous on the one hand, as the balloon can leave its place; on the other hand it can be unsuccessful when the fluid flows out of the balloon. Filling a quickly hardening fluid in the catheter ensures the stable fixing of the balloon in the vessel and a permanent, safe occlusion of the desired area.

The object of the present invention is to provide a novel and useful therapeutic equipment by which the above detachment and thus the embolization of certain vessels and permanent blocking of further ducts, respectively, can be performed easily and with great certainty without any problems at imparting the catheter.

The above balloon catheter method has been theoretically worked out recently by F. Sorbinenko [J. of Neurosurgery 41, 125-145 (1974)]. No material has been found, however, which allowed that the catheter could be detached effectively. Moreover, in the absence of the contrast material the position of the catheter could not be followed.

P. Schaps in Zentralblatt fur Neurochirurgie 38, 105-10 (1977) describes the use of silicon together with a microcatheter and a balloon. However, the viscosity of the material used was so high that only ice-cooling technique could be applied. Moreover, this material contained no X-ray contrast material.

G. Debrun, P. Lacour, J. Caron et al. [J. of Neurosurgery 49, 635-49 (1978)] describe similar methods. They report, however, difficulties with the impartation. In operations, detachment could be performed by using a coaxial catheter and thus, the technique could not be used with safety for the intracranial vascular free operations.

S. K. Hilal, P. Sane, W. J. Michelson and A. Kossein, Neuroradiology 16, 430-33 (1978) describe the use of silicon elastomer (Silastic 382), methyl silicon oil and tantalum powder in the microcatheter technique. The disadvantage of said mixture was the much higher viscosity than was good for an easy injection, and on the other hand the use of tantalum powder, as X-ray contrast material obstructed the catheter by forming plugs. Moreover, the tantalum powder is toxic.

In summary, there was no material available which corresponded to all the requirements as discussed above. These requirements are as follows:

1. The low viscosity is very important: the material should be pressed through a catheter of 0.1 mm. inner diameter and 150 mm. length. This requirement is very hard to provide, considering that the fluid injected should harden within a short period.

2. Due to the limited time for operations, the material should harden within a short time (i.e. 10 to 20 min.) so that sufficient time to inject the mixture (min. 3 to 4 min.) should also be provided.

3. The material should evenly fill in the catheter with sufficient plasticity so that no bubble is allowed to occur.

4. After hardening, however, the material should be rigid to a certain extent, i.e. it should break at the detachment point.

5. It is very important for the precise dosing and control that the material should also give X-ray shadow. This characteristic provides that the position of the catheter and balloon, respectively, can be followed.

6. Sterility, no toxic effect.

SUMMARY OF THE INVENTION

The silicon rubber mixture of the present invention consists of two-three components, respectively, one of which gives X-ray contrast. The therapeutic set according to the invention comprises a silicon rubber mixture, the catalyst for the polymerization of the mixture, as well as a microcatheter provided in a given case with an inflatable balloon catheter used for cerebral and other vessels and glandular ducts.

A further subject of the invention is the use of the new silicon rubber mixture and therapeutic set, respectively, in different fields of therapy, for the first time in cerebrovascular operations, vascular surgery, etc.

The silicon rubber mixture provided by the invention, forming component A of the therapeutic set fulfills all the above requirements.

DETAILED DESCRIPTION OF THE INVENTION

The silicon rubber mixture of the present invention consists of an appropriate mixture of two different fluid polysiloxanes and a non-toxic, physiologically acceptable contrast material.

Thus, the silicon rubber mixture according to the invention consists of the following components:

(a) a linear polysiloxane of low viscosity, preferably e.g. the so-called reactive silicon oil, i.e. a dialkyl-, alkylaryl-, alkenylalkyl- or diarylpolysiloxane which may contain reactive functional terminal groups, i.e. hydroxy, acyloxy, alkoxy or amino. Preferred polysiloxane is the dimethyl-polysiloxane-$\alpha$, $\omega$-diol, the so-called "LMS". Physical data of the said compound are as follows: $\bar{n}=80-85$, $\bar{M}=6-7000$, $d_4{}^{25°}$ C.$=0.976$ g./cm$^3$, $n_D{}^{25°}$ C.$=1.4043$, $^{25°}$ C.$=80-100$ m.Pa.s. (cP).

(b) A cyclic dialkyl-polysiloxane, which has a very low viscosity. Such a cyclic dialkyl-polysiloxane derivative may be e.g. a dialkyl-polysiloxane, e.g. the so-called $D_4([R_2SiO]_4)$ or $D_5([R_2SiO]_5)$. For purposes of the invention the $D_4$ is highly preferred. Its sturcute is $[(CH_3)_2SiO]_4$, the octamethyl-cyclotetrasiloxane, the physical data of which are as follows: $M=296$, b.p.$=175°$ C./0.1 MPa, $d^{20°}$ C.$=0.9558$ g./cm$^3$, $n_D{}^{20°}$ C.$=1.3968$, $_{20°}$ C.$=2$ mPas (cP).

The viscosity of the mixture of the linear and cyclic polysiloxanes should be between 10 and 100 mPs, at $_{25°}$ C. depending on the desired field of use.

(c) The mixture contains in a given case, methyl-silicon oil of a viscosity of 5 to 20 mPas which serves also to lower the viscosity.

(d) The fluid contrast material to be added to the mixture may be a physiologically acceptable silicium organic compound, which contains the iodine atom(s) giving the X-ray shadow built into a molecule. According to the invention, preferred contrast material is the bis-iodomethyl-tetramethyl-disiloxane. The iodine atom gives also the possibility of isotope labeling the material, when using e.g. I-131. The physical data of the said compound are as follows: $M=414$, b.p.$=134°$ C./1333,22 Pa, $d_4{}^{20}=1.172$ g./cm$^3$, $n_D{}^{20}=1.5263$. Mixtures of a viscosity of higher than 100 mPas may also be applied and non-metallic iodine-containing organic X-ray contrast materials in extracted, solid or fine form may also be used. Such materials are used in the angiological diagnostics and are commercial products, i.e. Amipaque, Uromiro, etc. These materials are to be added to the above components in ground homogenized form. However, use of such materials is difficult and requires more attention and the particle size should be chosen in accordance with the field of application so that the particles do not obstruct the microcatheter and in the case of free embolization the particles do not get into the capillar vascular system.

The silicon rubber system according to the invention, i.e. the component of the therapeutical set contains the linear polysiloxane mentioned above under paragraph (a) and should contain at least one of the materials under paragraphs (b) and (d).

The therapeutic set contains beside the component A mentioned above, the component B which can be any of the catalysts used for medical purposes in polymerizing cold-vulcanizing gums characterized by providing a fluidity of 8 to 10 min and a hardening time of 20 to 25 min.

It has been found that under the prescribed heat sterilizing conditions (120° C. for 30 mins) both components contain the original chemical characteristics and the ability to polymerize. Furthermore, the materials are acceptable in bacteriological aspects.

A further element of the therapeutic set is the microcatheter. Depending on the field of use, it may contain one or more lumina. The therapeutic set of the present invention may also contain, beside components A and B and the microcatheter, a balloon head made generally of natural silicone latex. This head has the importance for the first time in endovascular embolization wherein the silicon gum component is vulcanized in the ballon by the effect of the catalyst, thus forming a plug for blocking the said vessel. During free embolization, however, the use of balloon is not essential unless the wanted vascular area is not available otherwise.

The therapeutic set can be used as follows:

The microcatheter, provided in a given case with the balloon at its end, is led up to the target vessels or other duct-section. Then components A and B are ground and mixed to provide a homogenous mixture and the necessary amount is injected into the catheter through a calibrated tuberculin syringe. The injection is controlled by an X-ray fluoroscopic screen. After the rest of the material has hardened, the catheter is detached from the balloon head by a light, shifting and pulling. Subsequently the catheter is removed from the artery together with the silicon rubber vulcanized in the catheter.

Another object of the invention is the use of the said silicones and the mixture thereof for pharmaceutical purposes. The new material has been provided for the endovascular operation technique for the first time. The material and equipment may be used, however, in any case wherein no direct surgical intervention is possible or external operative approach of the concerned vessels is not advised.

The most important fields of the endovascular superelective embolization by means of balloon catheter are indicated among other as follows:

1. Blocking arteriovenous fistulas,
2. Embolization of arteriovenous angiomas,
3. Embolization of feeding arteries of highly vascularized tumors in order to promote the direct surgical removal of such neoplasms.
4. Endovascular occlusion of arterial saccular aneurisms.
5. Blocking outlet duct systems of different exocrin glands.

As mentioned, the embolization can be carried out by building the balloon into the vessel or other duct section to be blocked. The embolization may be performed, however, in the form of the so-called "free embolization" wherein the mixture of the components A and B according to the invention are injected directly into the pathological vascular area to be blocked, respectively, and the material is vulcanized in the vessel itself. It has been found that the materials and mixture of the invention are non-toxic either in themselves or during vulcanization. Thus, a further aspect of the present invention is the use of the materials and the mixture, respectively, described above, in the free-embolization technique.

Based on animal tests, the above materials were used in about 30 successful human operations within a period of one and a half years in cases which could not be operated directly. It was proved that the hardened silicon remained in the natural rubber balloon resulting in a definitive occlusion of the target spot. Following the X-ray shadow, the position of the balloon can be seen by a simple X-ray control even years after the operation. In the case of free embolization the position of a polymerized silicon rubber can also be controlled. It has also been found that the materials of the present invention, such as other silicones widely used in the surgery (i.e. ventricule-atrial shunts, articular and other plastics, dental materials, etc.) are entirely compatible and non-toxic. No infection or abnormal histological reaction could be detected. Essentially it is this characteristic which makes possible the free embolization method described above.

The following are examples for the silicon rubber mixture of the present invention.

EXAMPLE 1

Component, A 10 g of dimethyl-polysiloxane-$\alpha,\omega$-diol, viscosity 50 to 2000 mPas. 1 g. of powdered, dried X-ray contrast material (UROMIRO), passed through a sieve of a size of 0.65 $\mu$m.

The mixture is homogenized, and, before use, sterilized in vials. Compound B, the catalyst, 1,5 ccm of T-5 (Wacker dental catalyst product) is also sterilized in vial. Mixing of the two components provides a "batch-time" of 8 mins and a polymerization time of 15 mins. The catheter can be imparted after 15 to 25 mins.

EXAMPLE 2

Another possible component A is as follows: 10 g. of dimethyl-polysiloxane-$\alpha,\omega$-diol, viscosity 100 mPas, 2 g. of X-ray contrast material as in Example 1, 2 g. of methyl-silicon oil of dimethyl-polysiloxane basis, viscosity of 19 mPas. The catalyst component B and the amount thereof is the same as in Example 1.

EXAMPLE 3

Component A 2.5 g. of dimethyl-polysiloxane-$\alpha,\omega$-diol, viscosity 100 mPas, 2.5 g. of $D_4$ (cyclic polysiloxane), viscosity 4–5 mPas, 0.75 g. of bis-iodomethyl-tetramethyl-disiloxane (fluid iodo-containing X-ray contrast material). The misture is homogenized, and then filled into vials and sterilized. As component B, T-5 or T-11 catalysts (Wacker dental catalyst product) may be used in an amount of 1 ccm.

CLINICAL TESTS 1. 35 year old man, miner. After craniocerebral trauma, he developed an extreme large fistula between the right internal carotid artery and cavernous sinus, resulting in typical eye-symptoms, bruit, headache, lesion of the right II., III., IV- and both VI. cranial nerves. Via percutan endovascular catherization the fistula had been closed with 2 detached, siliconized balloons. Excellent clinical result, the patient is symptom-free even two years after the operation.

2. 25 year old man, electrotechnician. Severe subarachnoidal bleeding, resulted in transient unconsciousness and hemiplegia on the left. The angiographies proved a congenital arteriovenous malformation of the right cerebral hemisphere. There was no possibility of direct surgical operation, because of the size of the angiom. Two main feeding arteries of the vascular malformation have been occluded with superselective balloonembolization. Significant clinical improvement: the patient can walk alone, is free of mental disturbance, continues his original profession, has married, and had no more hemorrhages since the operation.

3. 53 year old woman, teacher. Giant saccular aneurysms on the cavernous portion of the left internal carotid artery, resulted in an earlier subarachnoidal hemorrhage and actual lesion of the left III. cranial nerve. For a safe occlusion, both the parent vessel and aneurysmal neck has to be embolized with a large balloon filled with silicone. The transient postoperative hemiparesis and aphasia as well as the oculomotor paresis have improved, the patient is practically free of symptoms after a period of a year and a half.

4. 24 year old man. After frequent nasal hemorrhages and definitive obstruction of the nose, a large-size haemangiom of the face had been proved histologically. Because of the size and location, the direct surgical operation was unsuccessful. After the embolization of the feeding maxillar arterial branches we succeeded in subtotal surgical removal of this benign tumor.

Although this method has been applied up until the present only when a direct surgical approach was impossible or too dangerous, there is a real possibility to extend the indication for routine cases of the mentioned diseases too, with better results and less hazard.

We claim:

1. In a method of embolization wherein an occlusion is formed in the vascular system by the vulcanization of an embolization agent in situ the improvement comprising said embolization agent being a silicone rubber component having reactive functional groups selected from the groups consisting of hydroxyl, acyloxyl, alkoxyl, and amino; a cyclic dialkyl-polysiloxane and a pharmaceutically acceptable iodo-containing organosilicium or non-metallic organic X-ray contrast material, and a component B comprising an effective amount of a therapeutically acceptable cross-linking catalyst.

* * * * *